(12) United States Patent
Keresman, III et al.

(10) Patent No.: US 7,606,771 B2
(45) Date of Patent: Oct. 20, 2009

(54) DYNAMIC NUMBER AUTHENTICATION FOR CREDIT/DEBIT CARDS

(75) Inventors: Michael A. Keresman, III, Kirtland Hills, OH (US); Andrew J. Hartridge, University Heights, OH (US); Chandra A. Balasubramanian, Mentor-on-the-Lake, OH (US)

(73) Assignee: CardinalCommerce Corporation, Mentor, OH (US)

( * ) Notice: Subject to any disclaimer, the term of this patent is extended or adjusted under 35 U.S.C. 154(b) by 1364 days.

(21) Appl. No.: 10/044,630

(22) Filed: Jan. 11, 2002

(65) Prior Publication Data

US 2002/0120583 A1    Aug. 29, 2002

(51) Int. Cl.
H04L 9/00       (2006.01)
H04K 1/00       (2006.01)

(52) U.S. Cl. .............................. 705/67; 705/65; 705/75; 705/78; 705/64; 463/16; 463/17

(58) Field of Classification Search .............. 705/64–79, 705/2–3; 463/16–17
See application file for complete search history.

(56) References Cited

U.S. PATENT DOCUMENTS

| | | | |
|---|---|---|---|
| 4,799,156 A * | 1/1989 | Shavit et al. ................... 705/26 |
| 5,251,259 A | 10/1993 | Mosley |
| 5,251,636 A * | 10/1993 | Neuman ..................... 600/537 |
| 5,317,636 A | 5/1994 | Vizcaino |
| 5,450,491 A | 9/1995 | McNair |
| 5,478,994 A | 12/1995 | Rahman et al. |
| 5,544,246 A * | 8/1996 | Mandelbaum et al. ......... 705/65 |
| 5,590,038 A | 12/1996 | Pitroda |
| 5,627,355 A | 5/1997 | Rahman et al. |
| 5,657,388 A * | 8/1997 | Weiss .......................... 713/185 |
| 5,826,245 A * | 10/1998 | Sandberg-Diment ........ 705/44 |
| 5,867,821 A * | 2/1999 | Ballantyne et al. ............. 705/2 |
| 5,884,271 A | 3/1999 | Pitroda |
| 5,887,065 A | 3/1999 | Audebert |
| 5,892,900 A * | 4/1999 | Ginter et al. ................. 713/200 |
| 5,913,203 A | 6/1999 | Wong et al. |
| 5,937,344 A | 8/1999 | Wong et al. |
| 5,943,423 A * | 8/1999 | Muftic ......................... 705/67 |
| 5,956,699 A | 9/1999 | Wong et al. |
| 5,999,626 A | 12/1999 | Mullin et al. |
| 6,236,981 B1 * | 5/2001 | Hill .............................. 705/67 |
| 2002/0052762 A1 * | 5/2002 | Kobylevsky et al. ........... 705/2 |

* cited by examiner

*Primary Examiner*—Calvin Loyd Hewitt, II
*Assistant Examiner*—Cristina Owen Sherr
(74) *Attorney, Agent, or Firm*—Fay Sharpe LLP

(57) ABSTRACT

A method and apparatus for conducting a commercial transaction over the Internet or other network connection are provided. The method includes the use of random numbers which are unique for each user session. These random numbers are pre-loaded onto a handheld, portable device, token, at the time of the device's manufacture or programming. These numbers are generated by external systems. The external systems then deliver the number sets to the token for storage in the token's internal memory and also to another random number database that is accessible by an authentication system. The random numbers are dispensed by the token to a user by pressing a button on the token or otherwise signaling the token. A simple polynomial equation may be employed in order to increase the number of codes. A dispensed number is cross referenced, by the authentication system, to the random number database that was created when the token was programmed. In this way the user or transaction can be authenticated. In its preferred configuration, it is intended that once the total number of random combinations, including the original random numbers and numbers generated by polynomial transformations, have been exhausted, the device becomes inoperable.

19 Claims, 6 Drawing Sheets

DYNAMIC NUMBER AUTHENTICATION FOR CREDIT/DEBIT CARDS

FIELD OF THE INVENTION

This invention is directed to the provision and dispensing of unique, random number sets for a variety of transactional applications and, in particular, to applications using random numbers for authentication purposes. It finds application in conjunction with network based and, more traditional, face-to-face transactions.

BACKGROUND OF THE INVENTION

One type of network transaction is Internet commerce. Other applications include voting online, accessing medical records, interacting with the government, etc. A common requirement for all of these applications is a reliable method for authenticating the user in order to prevent unauthorized access to sensitive or important data.

Internet commerce, or e-commerce as it is otherwise known, relates to the buying and selling of products and services by buyers and sellers over the Internet or the transactional exchange of information. The convenience of shopping over the Internet has sparked considerable interest in e-commerce on behalf of both buyers and sellers. Internet sales, or like transactions, have been typically carried out using standard credit or debit cards such as Visa®, MasterCard®, Discover®, American Express®, or the like. However, while widely used for more traditional face-to-face transactions, use of these standard credit or debit cards in connection with e-commerce presents certain difficulties. For example, maintaining buyer confidence and security has become difficult with increased reports of credit card fraud. The resulting apprehension is also fueled by buyer uncertainty of the reputation or integrity of a seller with whom the buyer is dealing. The security of the buyer's credit card information or other personal information (e.g., address, credit card number, phone number, etc.) typically submitted along with a traditional Internet credit card transaction serves to increase the apprehension even more. Additionally, credit card account holders, sellers and financial institutions are concerned about safeguarding against fraudulent or otherwise unauthorized credit card transactions.

It would be desirable, therefore, to provide a new method for carrying out authenticated credit or debit card transactions in particular, and any transaction requiring authentication in general, over the Internet and in the face-to-face world that overcomes the above-described problems.

SUMMARY OF THE INVENTION

The present invention comprises a method and apparatus for conducting a commercial transaction over the Internet or other network connection. The method includes the use of random numbers which are unique for each user session. These random numbers are pre-loaded onto a handheld, portable device, hereinafter referred to as a token, at the time of the token's manufacture or programming. These numbers are generated by external systems (computer systems or other random number generating devices). The external systems then deliver the number sets to the token for storage in the token's internal memory and also to another random number database that is accessible by an authentication system.

Generating the numbers on an external system relieves the token of a significant amount of computational overhead. By reducing the computational overhead, energy savings are realized that enable the token to use smaller, less powerful energy sources.

The random numbers are dispensed by the token to a user by pressing a button on the token or otherwise signaling the token. Optionally, the token may need to be activated by using a secret PIN (personal identification number) that was assigned to, or chosen by, the user at the time of registration. In order to increase the number of random codes that are available to an authentication system, simple polynomial equations may be employed to transform each random number into one or more additional numbers. A dispensed number is cross referenced by the authentication system to the random number database that was created when the token was programmed. In this way the user or transaction can be authenticated.

In its preferred configuration, it is intended that once the total number of random combinations, including the original random numbers and numbers generated by polynomial transformations, have been exhausted, the token becomes inoperable.

While the token can take on any of numerous forms, in a preferred embodiment, the token takes on the form of a credit card. This preferred form is essentially the size of a traditional credit card in width, height and thickness. This credit card form is, optionally, solar powered and has internal magnetic transducers that allow the token to emulate a credit card magnetic strip. Other forms include software loaded on cellular phones, computers or Internet enabled appliances.

It is an advantage of the present invention that exposure of a user's credit card information on a network connection is reduced or eliminated, and a user can carry out a transaction on a network with simplified encryption methods, or even without encryption.

It is another advantage of the present invention that computational requirements, and resultant energy needs, are minimized on the token.

It is yet another advantage of the present invention that the token can be used in face-to-face transactions where a credit card scanner, or other magnetic strip scanner, is used.

It is still another advantage of the present invention that a single token can authenticate multiple accounts, eliminating the need to carry multiple cards such as credit cards, debit cards and other similar cards.

DESCRIPTION OF THE DRAWINGS

The present invention exists in the construction, arrangement, in combination of the various parts of the device, and steps of the method, whereby the objects contemplated are attained as hereinafter more fully set forth, specifically pointed out in the claims, and illustrated in the accompanying drawings in which:

DETAILED DESCRIPTION OF THE PREFERRED EMBODIMENTS

Figure 1B:
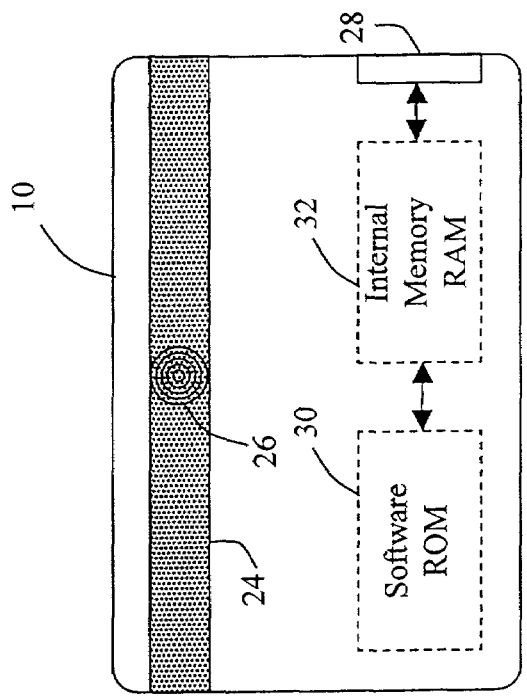
FIG. 1b illustrates the back side and internal memory of an aspect of a preferred embodiment of the present invention.

In accordance with one aspect of the present invention, a method for conducting a commercial transaction over the Internet or other network connection is provided. The method includes the use of random numbers (non-predictable numbers that are not deliberately mathematically related to any other number generated or dispensed by the device) which are unique for each user session. In a preferred embodiment, these random numbers are pre-loaded onto a handheld, portable device, hereinafter referred to as a token, at the time of the token's manufacture or by programming the token at a later time over a network connection. In alternate embodiments, the random numbers are pre-loaded onto other devices such as personal computers (PCs), notebook computers, handheld computers, personal data assistants (PDAs), web pads, net appliances and cell phones. The description provided hereinafter is directed primarily to an aspect of the invention incorporating the token, however, it is to be understood that the method described applies equally well to the aforementioned alternate devices.

The random numbers are generated by external systems (computer systems or other random number generating devices). The external systems then deliver the number sets to the token for storage in the token's internal memory and also to another random number database that is accessible by an authentication system, serving as an authentication agent, which may optionally be the same system as the random number generating system.

The random numbers are dispensed by the token to a user upon demand. The user requests a number to be dispensed by pressing a button on the token or otherwise signaling the token. In order to increase the number of random codes that are available in the token, one or more simple polynomial equations may be employed as transformation functions, producing additional numbers from each random number. For example, each stored random number can be first transformed by a first polynomial equation, and the transformation result dispensed to the user. A subsequent user request for a number can cause the untransformed number to be dispensed. This method doubles the number of codes available on the token. If polynomial transformations are implemented, each random number can be transformed by 1 to N polynomial equations, effectively increasing the number of available codes by a factor of N+1. A dispensed number is cross referenced, by the authentication system, to the random number database that was created when the token was programmed. In this way the user or transaction can be authenticated.

It is intended, in a preferred configuration, that once the total number of random combinations, including the original random numbers and numbers generated by polynomial transformations, have been exhausted, the token becomes inoperable. Alternately, the token may be reloaded with a new set of numbers.

The token can take on any form suitable for a given application. For example, the token can be a small handheld device similar to a small calculator. In a preferred embodiment, however, the token takes on the form of a credit card, debit card or similar card. This form is essentially the size of a traditional credit card in width, height and thickness. The token is, optionally, solar powered and has internal magnetic transducers that allow the token to emulate a credit card magnetic strip. This allows the token to be used for face-to-face transactions that traditionally use a magnetic card reader. Other physical devices that may be employed are, but are not limited to, wrist watches, cellular phones, key chain fobs, etc. The token can, therefore, be used for multiple types of transactions such as, for example, debit transactions, accessing credit lines, accessing personal records, etc.

Figure 1A:
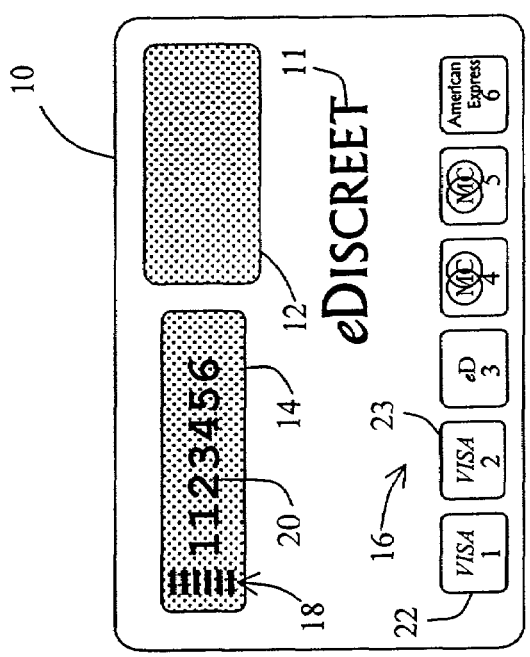
FIG. 1a illustrates the front side of an aspect of a preferred embodiment of the present invention.

With reference to FIG. 1*a*, the front side of a token 10 is shown. Visible on the front side of the token 10 are a logo 11, a power source 12, a display area 14 and buttons 16. Included in the display area 14 are a status indicator 18 and a dispensed number 20. In a preferred embodiment, each of the buttons 16 is used to select an account and request that the token 10 dispense a random number from its internal memory. For example, a first button 22 is configured to select a first Visa® account. Upon detecting a selection of the first button, software in the token selects the next available number from its internally stored numbers, "123456" for example, causes a code representing the selected Visa® account to be displayed, "1" for example, combined with the selected number in the display area 14, "1123456" in this example, and deletes the selected number from its internal memory or, alternately, advances a pointer to the next available number. In either case, only unused numbers remain available for succeeding selections of the buttons 16.

If, as an alternate example, a second button 23 is selected, a different code representing a second Visa® account, "2" for example, is combined with the selected number in the display area 14, "2123456" in this alternate example. Each of the buttons 16 has a unique code assignment depicting a type of account as illustrated in the previous example. The code representing the selected account may be a prefix as in the aforementioned example or, alternately, the code may be displayed as a suffix, or as an intermediate portion, of the dispensed number 20. Alternately, the selected random number can be prefixed or suffixed to the user's account number, or other account identification, provided by the issuing financial institution. The status indicator 18, configured as a bar graph in this example, is updated to indicate visually the quantity of numbers remaining in the token.

In a preferred embodiment one table of numbers is programmed and shared by all of the buttons 16 and the bar graph status indicator 18 provides an indication of the total quantity of random numbers remaining in an internal memory 32. When the token 10 is initially programmed with a set of random numbers, the bar graph is displayed at a maximum height as illustrated in FIG. 1*a*. As the internal memory 32 becomes depleted of numbers after each use of the token 10, the bar graph becomes shorter in proportion to the percentage of originally programmed random numbers remaining. If, however, multiple tables of random numbers are programmed into the memory 32, one table for each of the buttons 16 for example, the token 10 is configured to display a bar graph indicative of the percentage of numbers remaining for the most recently selected button.

While FIG. 1*a* is directed specifically to a token device, all of the features presented therein can be incorporated into a software embodiment for use on interactive devices capable of displaying a graphical representation of FIG. 1*a* on a graphical display screen, wherein physical buttons are replaced by virtual buttons. For example, PC software can simulate the token 10 with a graphical likeness of the token, wherein a pointing device such as a mouse is used to select one of the buttons 16. Similarly, notebook computers, handheld computers, PDAs, web pads, net appliances and cell phones with GUI capabilities can incorporate software embodiments of the present invention.

Cell phones that have only a text capable display screen can, however, simulate the features of the token 10 with a text based interface. For example, the cell phone displays a text line representing the logo 11, followed by additional text lines representing each of buttons 16, wherein each text line also displays a number associated with each button. A user then uses the cell phone keypad to select one of the buttons by entering the number corresponding to the desired button.

The front side of the token 10 as shown in FIG. 1a includes an exemplary logo 11, "eDiscreet" as shown. The token 10 can, however, be a privately labeled token. For example, a bank such as Key Bank could use the token to access Key Bank accounts. In this case, the token would display a logo 11 representing Key Bank. The logo would, in general, be a logo selected by the financial or other institution to which a particular token 10 is tailored.

In FIG. 1b, with continuing reference to FIG. 1a, the back side of the token 10 is shown. Visible on the back side of the token are a simulated magnetic strip 24 which serves as an aid in orienting the token correctly for scanner devices, a magnetic transducer 26 for generating pulses suitable for reading by scanner devices, and a communications port 28 for programming the token. Also shown are an internal software memory 30 for the aforementioned software and an internal memory 32 for storing random numbers. In a preferred embodiment, the internal memory 32 is implemented as a non-volatile memory so that, during times when the power source 12 is not providing energy, numbers are not lost from memory 32. Software memory 30 may be implemented as read-only memory (ROM) or, alternately, as a non-volatile, programmable memory.

Figure 2:
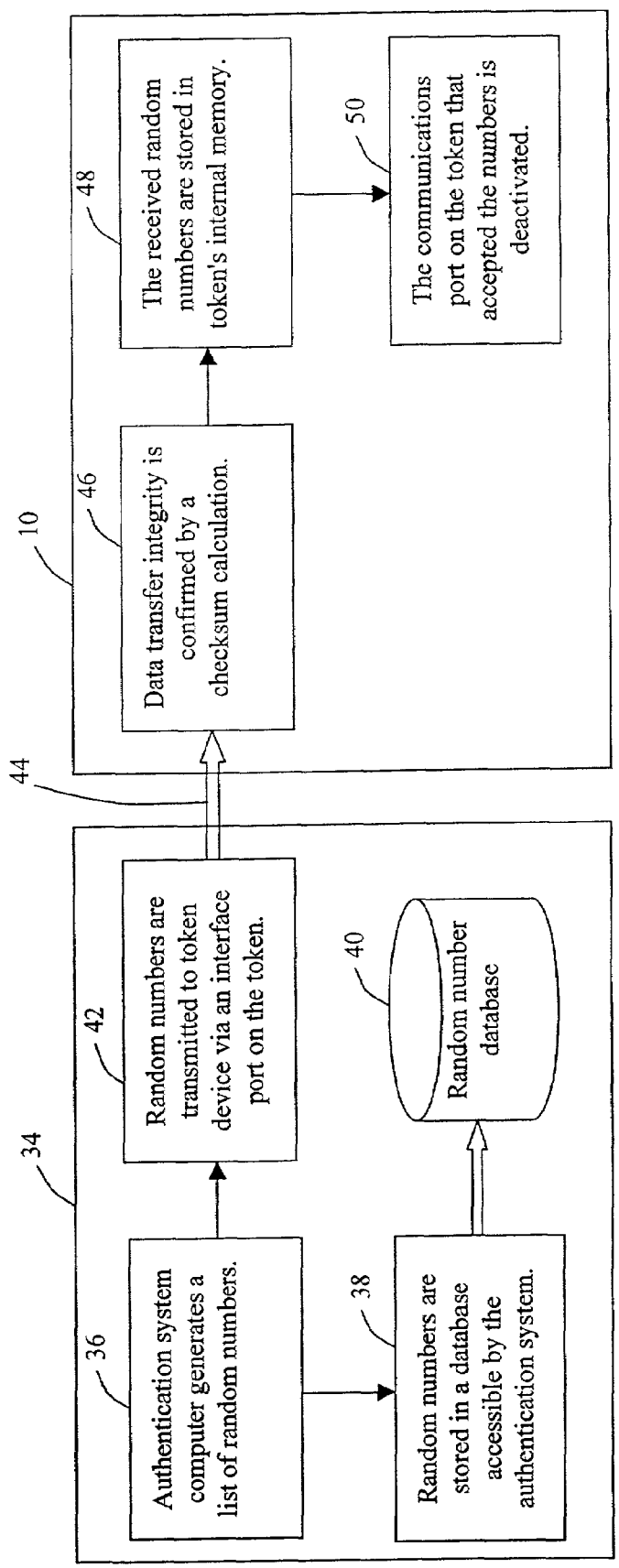
FIG. 2 is a flow diagram showing a method of programming a token with random numbers.

With continuing reference to FIGS. 1a and 1b, a method of programming the token 10 with a unique set of random numbers is illustrated in FIG. 2. An external authentication system 34 is configured to generate unique sets of random numbers by any of a number of well known means. Within the system 34, an authentication computer 36 calculates a predetermined quantity of random numbers which are subsequently stored by a function 38 in a random number database 40. The program 42 also transmits the random numbers over a communications link 44 to the communications port 28 on the token 10. The software in memory 30 verifies the integrity of the random number transmission with a function 46, stores the random numbers in the internal memory 32 with a function 48, and deactivates the communications port 28 with a function 50 to prevent alteration of the stored random numbers.

Because a cell phone communicates via a cellular network and is occasionally out of the service range of the network for extended periods of time, it is desirable that the cell phone is programmed with a smaller set of random numbers than the token 10, or software versions on personal computers and similar devices, and that the cell phone is also configured to allow a user to request a new set of random numbers from an authentication system as needed. Personal computers and cell phone embodiments may optionally be reloaded with a set of random numbers over the Internet or cellular network, respectively.

Figure 3:
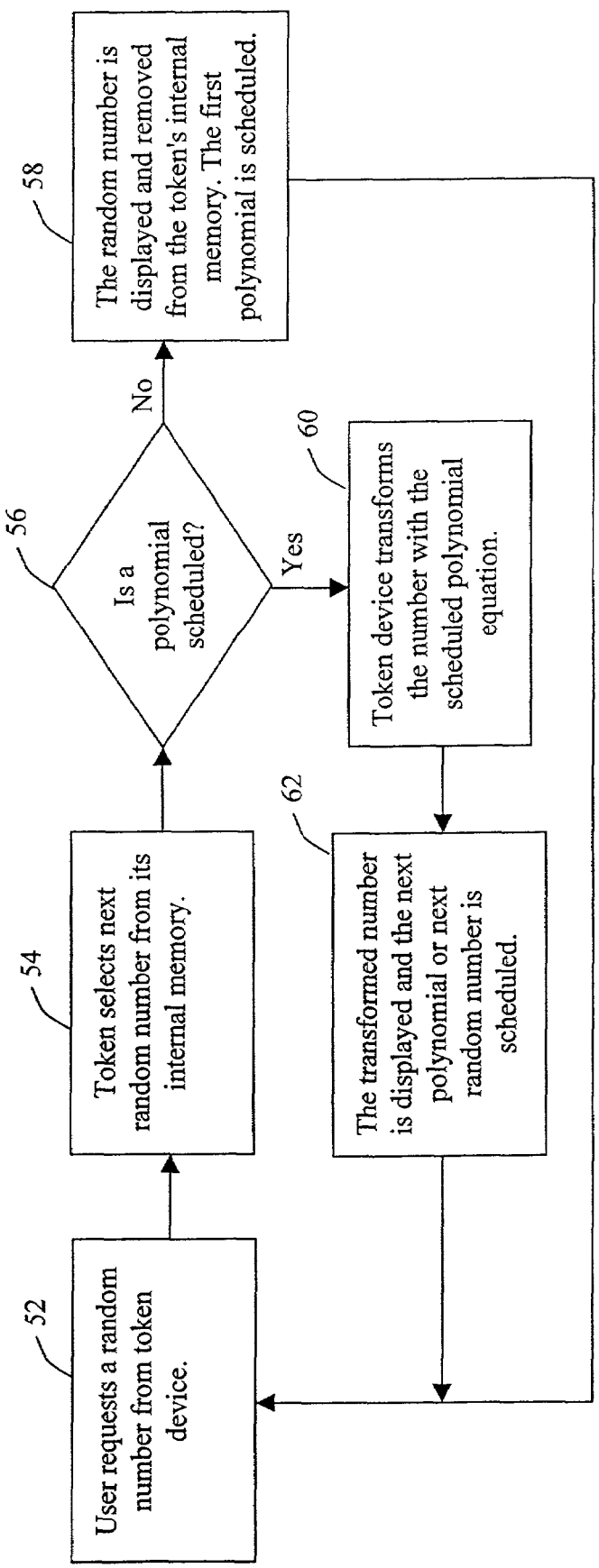
FIG. 3 is a flow diagram of a method of dispensing random numbers from a token.

As previously mentioned, the token 10 dispenses numbers to a user upon demand. A method of dispensing random numbers from internal memory 32 is shown in FIG. 3. The user requests a number to be dispensed by pressing one of the buttons 16 on the token at step 52. Subsequently, at step 54, the software in memory 30 selects the first available random number from the internal memory 32. Because polynomial transformations can be employed by the present invention, a decision at step 56 is made to determine if a polynomial transformation is scheduled for the currently selected random number.

If there are no remaining predefined polynomial transformations to be applied to the selected number, processing continues at step 58 where the selected number is displayed in the display area 14 as the display number 20 and removed from the token's internal memory 32. Preferably, the displayed number 20 includes at least one indicator digit depicting which of the buttons 16 was selected, for example, a prefix code representing the selected Visa® account as shown in FIG. 1a. This code is used by the authentication system 34 to determine which account to use when processing the transaction. The first of the predefined polynomials is then scheduled, and processing returns to step 52 to await another user request. If a polynomial is scheduled, step 56 causes processing to continue at step 60 where software in memory 30 applies the scheduled polynomial transformation to the number. At step 62, the transformed number is displayed with the aforementioned indicator digit. At step 62, the next polynomial transformation is scheduled or, if no more polynomials remain, an indicator is set to control the next execution of step 56.

It should be noted that, when polynomial transformations are implemented, the above-described method applies the polynomials to each random number selected from internal memory 32 and displays the untransformed number after all transformations are applied. Software in memory 30 can, however, be configured to display the untransformed number before applying any transformations, or can also be configured to display the untransformed number at any intermediate point as well.

Figure 4:
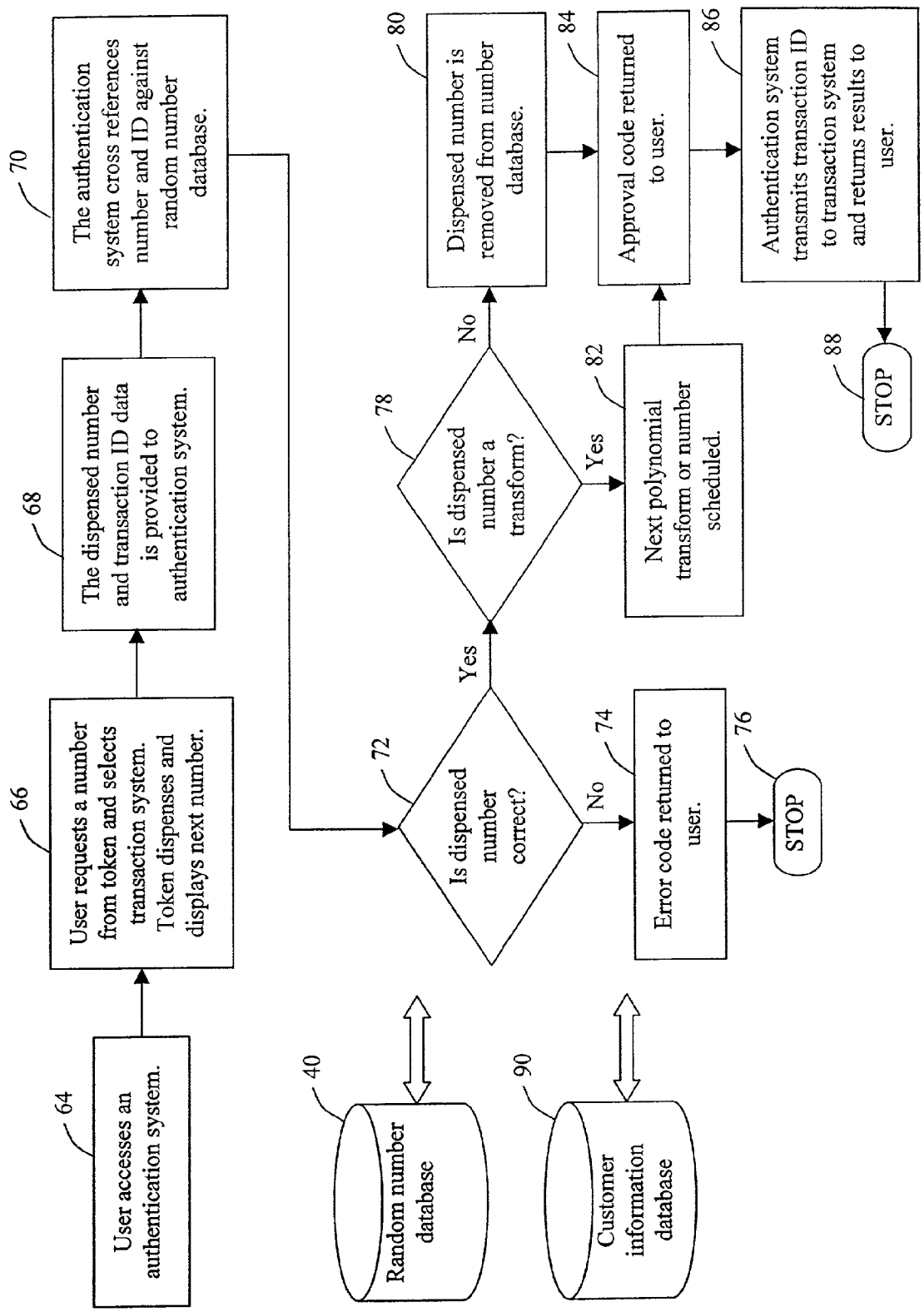
FIG. 4 is a flow diagram showing a method of user authentication suitable for implementation in the present invention.

A method of processing an authenticated transaction, a credit or debit card purchase for example, is illustrated in FIG. 4. At step 64, a user accesses the authentication system 34 by any well known means, a dial-up internet connection for example. The user then requests a number from the token 10 at step 66, and at step 68, the token dispenses, by the method shown in FIG. 3, a number including an indicator digit as previously described. The user next communicates this number and other account identification data (e.g. a user ID or name) to the authentication system 34 and, at step 70, the authentication system cross references the number and the user's ID against the random number database 40.

A decision is made at step 72 as to whether the supplied number is correct or incorrect. If the number is incorrect, an error code is returned to the user at step 74, and processing stops at step 76. If the number is correct, that is it matches the first available number for the user in the database 40, processing continues at step 78 where it is determined if the supplied number is the result of a polynomial transformation. If the number is not the result of a transformation, the number is removed from the database 40 at step 80, otherwise, the next polynomial transformation is scheduled at step 82 in a manner equivalent to the method shown in FIG. 3. In either case, an approval code is returned to the user at step 84. At step 86, the authentication system 34 transmits the user's account identification and card number to a transaction system associated with the above-mentioned indicator digit.

In order to reduce, or eliminate, exposure of a user's account information to other users of a network, it is also provided that the authentication system 34 can optionally maintain the user's account numbers and validating data such as card expiration dates in a customer information database 90. A user of the authentication system 34 then is not required to submit his or her account number for each transaction. Instead, at step 86, the authentication system 34 can be configured to select the user's account information from the customer information database 90 for transmission to the selected transaction system.

To eliminate exposure of the user's account information to the network, alternate methods can be employed. For example, the authentication system 34 may, alternately, make any required payment, from funds available to the authentication system, to the transaction system requesting payment, thereby eliminating exposure of the user's account information to the network. In this alternate embodiment, the authentication system 34 subsequently debits the user's account directly.

Another possibility is that a user who is connected to an online merchant over the Internet will have an established account with the online merchant, and the online merchant will be connected through a secure line, such as a private leased line, to an authentication system 34 serving as an authentication agent. In this case, the online merchant will have the user's credit card or debit card account information on file and, therefore, only needs to request a random number from the user's token 10 for authentication purposes. The online merchant then communicates the random number to the authentication agent for verifying that the connected user is the legitimate account owner. The online merchant then completes the financial transaction through a secure line, either through the authentication agent, or directly to the financial institution holding the account.

With sensitive data stored on the database 90 and not being supplied by a user over a network to the authentication system, it becomes feasible to use a simplified encryption function for submitting dispensed numbers to the authentication system 34. The risk associated with theft of a transmitted number is reduced because each dispensed number is used only once and becomes useless thereafter. Without exposure of the user's account information to a network connection, it is feasible to carry out a transaction on a network without encryption.

The authentication method described in FIG. 4 assumes that the token 10 remains synchronized with respect to the random number database 40 by deleting each number, as it is used, from the random number database and the token's internal memory 32. It is also envisioned that synchronization may be accomplished by means of pointers in the database 40 and internal memory 32 where each pointer is incremented as each number is used. With either method of synchronization, however, it is useful to have a means of resynchronization. For example, a user may inadvertently select one of the buttons 16 causing the token 10 to dispense a number that is not needed by the user, thus causing internal memory 32 to advance one number ahead of the database 40 for each such occurrence.

Figure 5:
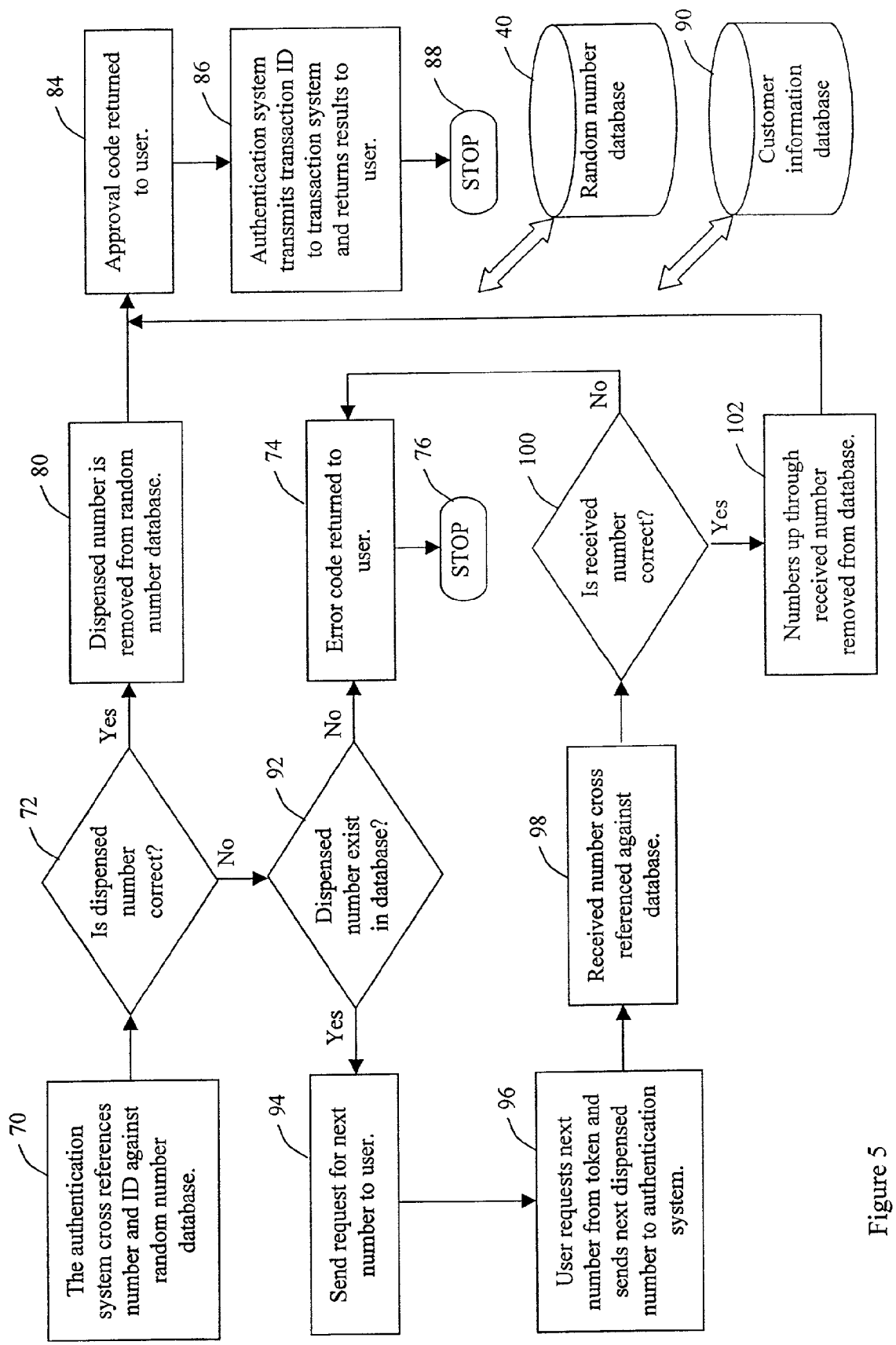
FIG. 5 is a flow diagram showing a method of synchronizing a random number database and a token; and, FIG. 6 illustrates the front side of an alternative embodiment of the present invention incorporating PIN numbers.

FIG. 5 shows an alteration to the method of FIG. 4 that permits resynchronization to occur. It is assumed for the sake of simplicity that no polynomial transformations are implemented in FIG. 5, however, suitable alterations to FIG. 5 are easily imagined by comparison with FIG. 4. Like numbered steps in FIG. 5 correspond to identical steps in FIG. 4. For example, FIG. 5 starts at step 70 where the authentication system cross references the supplied number and the user's identification against the random number database 40. Steps 72, 80, 84, 86 and 88 perform functions equivalent to the same numbered steps in FIG. 4 and, therefore, require no further description. The first difference with respect to FIG. 4 occurs when step 72 determines that the supplied number is not correct.

A negative answer in step 72 causes step 92 to be processed where it is determined whether the supplied number exists in the database 40 at some point after the next available number in the database. If not, processing continues at steps 74 and 76, as before, to report an error to the user. If, however, the supplied number does exist, an attempt is made to resynchronize the database 40 with the token 10 internal memory 32. At step 94, a request is sent to the user asking the user to provide the next available random number from his or her token's internal memory 32. The user, in turn at step 96, has his or her token dispense a second random number in the above-described manner and provides the number to the authentication system 34.

Upon receiving the next random number from the user, the authentication system cross references the number against the random number database 40 at step 98. A query is made at step 100 to determine if, in the database 40, the second number immediately follows the number originally supplied by the user. If this is the case, resynchronization is possible, and all random numbers in the database 40 to and including the second supplied number are removed from the database at step 102, and processing proceeds normally at step 84. If, however, resynchronization is not possible, processing continues at step 74 to report an error to the user. Suitable alterations to the method of FIG. 5 can be readily imagined to support polynomial transformations and other methods of tracking the next available number in the database 40, such as pointers for example.

As the available random numbers in the random number database 40 and internal memory 32 become depleted, alternate embodiments of methods exist for reminding a user that his or her token 10 is expiring and providing for replacement of the token. The status indicator 18 provides a visual indication to a user of the status of internal memory 32. Software in memory 30 is configured to update the status indicator 18 as each number is removed from internal memory 32. The status indicator 18, for example, serves as a bar graph depicting the remaining quantity of numbers available from internal memory 32. On the remote side, the authentication system 34 is configured to monitor the quantity of numbers available in the database 40 and can provide progressively more prominent warnings to a connected user as the database 40 becomes more depleted with each use. For replacement of an expired token 10, the authentication system 34 can optionally be configured to automatically trigger mailing of a new token 10 when the quantity of available numbers in the database 40, and the token, is reduced to a predetermined threshold value.

Another method for reminding a user that his or her token 10 is expiring, that may be used in place of or supplemental to the above-described methods, is to provide one or more "dummy" numbers at or near the end of the set of random numbers. For example, a number consisting of all nines could alert the user that replacement of the token in the near future is advisable. Also, the user could easily recognize that the number is a dummy number, and not one to be used for authentication purposes.

Although, in a preferred embodiment of the present invention, the token 10 becomes inoperable when memory 32 becomes depleted, the authentication system 34 can be configured to perform reprogramming of an expired token 10. For example, the communications port 28 can be reactivated when internal memory 32 becomes depleted, allowing for reprogramming of the token 10 as previously described with reference to FIG. 2.

Receiving random numbers from the authentication system 34 and storing the numbers in internal memory 32 offers advantages in terms of reduced software complexity for the software in memory 30, and in terms of reducing computational power. The calculating of random numbers is relatively complex when compared to a simple method of selecting the next available number from a table of stored numbers as described with reference to FIG. 3. The reduced computational complexity reduces the quantity of energy dissipated and provides the advantage of reduced battery or solar cell drain. The aforementioned simplified encryption function, or elimination of encryption, would further reduce battery or solar cell drain.

The reduced power requirements offered by the present invention make it feasible for the power source 12 to be implemented in the form of a solar cell. Although the term "solar cell" has been used here, it is intended that the power source 12 receive sufficient light from interior lighting to provide adequate power to the token 10. If the power source 12 is implemented in the form of a battery, the reduced power requirements make it possible to utilize a smaller battery which aids in keeping the size of the token 10 substantially similar to a standard credit card. Alternately, the power source 12 can be implemented as a solar cell, with a battery backup providing power during periods of low light intensity.

It is intended that the present invention can be utilized in face-to-face transactions in addition to remote transactions over a network. For this purpose the magnetic transducer 26 has been provided on the token 10. A typical credit card, debit card or other such card includes a magnetic strip in the position of the simulated magnetic strip 24. On this strip, account information is recorded magnetically as a series of binary bits in either a 0 or a 1 state. This account information is read by scanners in face-to-face transactions such as typically occur during over-the-counter purchases in retail establishments. The token 10 and the magnetic transducer 26 can be configured to simulate the typical magnetic strip of a credit card, debit card or similar card, enabling the use of the token in magnetic strip readers.

Software in memory 30 can be configured so that, while the dispensed number 20 is being displayed, the magnetic transducer 26, in a timed sequence, changes its polarity in accordance with a string of zeroes and ones representing the dispensed number 20, and/or any other information such as a predetermined account number. The timing of the sequence of zeroes and ones is configured such that the generation of zeroes and ones at the transducer 26 occurs at substantially the same rate as the passage of zeroes and ones through a scanning device during a typical credit card transaction.

Although the transducer 26 is generating the equivalent of zeroes and ones at a typical scanning rate, the zeroes and ones do not appear spatially across the strip 24 as they do on a typical credit card. Instead, the associated magnetic fields generated by the transducer 26 are sufficiently large in magnitude that a typical magnetic strip reader can sense the zeroes and ones if the transducer 26 is only in the vicinity of the reader. Therefore, it is possible for a user to pass the token 10 through a magnetic strip reader in a manner similar to a standard credit card. Several methods of ensuring that the transducer 26 operate when in the vicinity of the magnetic strip reader currently exist.

One method of ensuring operation of the transducer 26 when in the vicinity of a magnetic strip reader is to configure one of the buttons 16 to act as a trigger switch for the transducer, such that the transducer does not operate unless the configured button is selected. This method would reduce the power requirements of the token 10, eliminating unnecessary operation of the transducer 26. Alternately, software in memory 30 can be configured to operate the transducer 26 while the dispensed number 20 is being displayed. The operation of the transducer 26 can be repeated at intervals, with a suitable delay between intervals, so that a magnetic strip reader can sense the series of zeroes and ones when the token 10 is passed through the reader.

Figure 6:
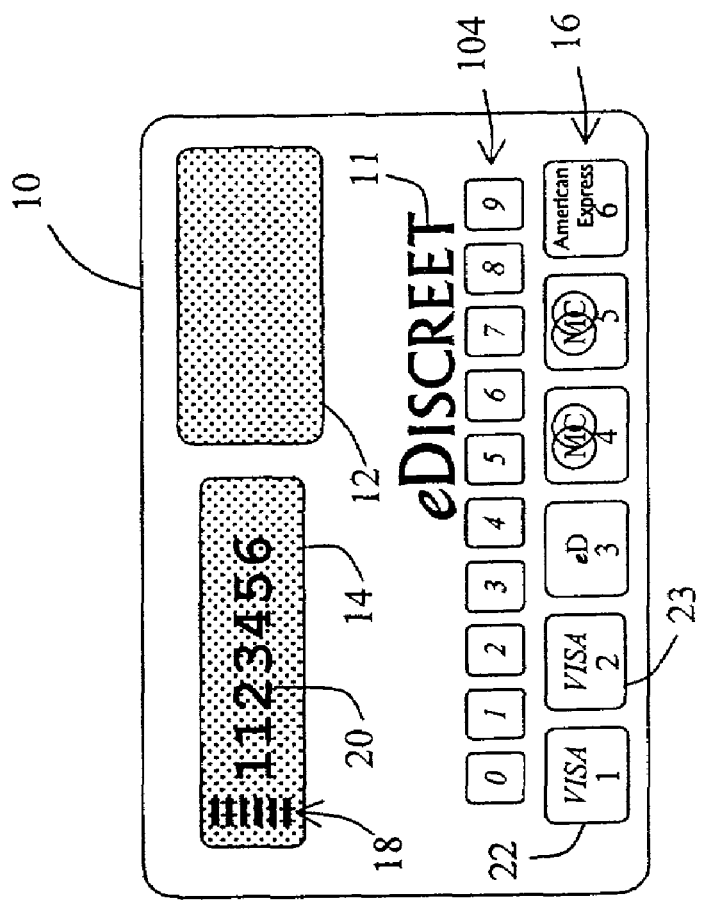

The embodiment as described in aforementioned FIGS. 1a and 1b can optionally be enhanced security-wise to include provision for a PIN number. A PIN number can be programmed into the token 10 as part of the programming of the token as illustrated in FIG. 2. Once the token has been programmed with a PIN number, upon selection of one of the buttons 16 by a user, the token requests that the programmed PIN number be entered by the user and software 30 is configured to not dispense a random number from memory 32 until the correct PIN number has been entered. FIG. 6 shows an embodiment including a set of numeric keys 104 for a user to use when entering a PIN number. Other arrangements of keys are possible. For example, the number of buttons 16 available can be made sufficient for entering a PIN number, wherein each of the buttons 16 is assigned a numeric value. In this case, after choosing an account by selecting one of the buttons 16, the user would select the correct combination of buttons comprising the programmed PIN number, and the token 10 would return to an appropriate state thereafter, either dispensing a random number if the entered PIN is correct, or waiting for another account selection if the PIN entered is incorrect.

The invention has been described with reference to the preferred embodiments. Obviously, modifications and alterations will occur to others upon a reading and understanding of this specification. It is intended to include all such modifications and alterations insofar as they come within the scope of the appended claims or the equivalents thereof.

What is claimed is:

1. A token for conducting commercial transactions comprising:
   a power source;
   a memory storing a unique set of predetermined random numbers and software, when executed causes the token to perform the steps of: selecting and dispensing an unused number from the set of predetermined random numbers, wherein the set of random numbers is identical to a set of numbers stored in an external authentication system;
   a plurality of buttons wherein each button is assigned a unique account identification number representing an account for conducting a commercial transaction, and said buttons for selecting and dispensing a previously unused number from the set of random numbers using the software; and
   displaying means for displaying the dispensed numbers and said unique account identification numbers.

2. The token for conducting commercial transactions according to claim 1 wherein the token becomes inoperable when the unique set of random numbers becomes exhausted.

3. The token for conducting commercial transactions according to claim 1 further including a communications port, wherein the token may be reprogrammed via the communications port with a new set of random numbers by an external system when the unique set of random numbers becomes exhausted.

4. The token for conducting commercial transactions according to claim 1 further including 1 to N predetermined polynomial transformation equations, wherein the 1 to N predetermined polynomial transformation equations operate on each random number to provide 1 to N additional numbers for each of the predetermined random numbers.

5. The token for conducting commercial transactions according to claim 1 further including a magnetic transducer, wherein the software is configured to cause the magnetic transducer to generate magnetic pulses according to the selected button for emulating the conventional magnetic strip of a standard credit/debit card and, wherein the magnetic pulses represent one of the dispensed random number with the unique account identifier and predetermined credit/debit card identification numbers programmed for each of the buttons.

6. The token for conducting commercial transactions according to claim 1 further including a PIN number, wherein the software is configured to request a user to enter the predetermined PIN number each time the token is activated, and wherein the software is configured to not dispense a random number until the correct PIN number has been entered.

7. The token for conducting commercial transactions according to claim 6, wherein the PIN number is entered by selecting the appropriate buttons, and wherein there are sufficient buttons to represent each digit of the PIN number.

8. The token for conducting commercial transactions according to claim 6 further including a keypad, wherein the PIN number is entered by selecting appropriate keys on the keypad.

9. The token for conducting commercial transactions according to claim 1, wherein the power source includes at least one of a battery and a solar cell, and wherein the solar cell may optionally generate sufficient power from interior lighting.

10. A device for conducting commercial transactions comprising:
a power source;
first memory for storing a unique set of predetermined random numbers, second memory storing software when executed causes the device to perform the steps of: selecting and dispensing an unused number from the set of random numbers, wherein the set of random numbers is identical to a set of numbers stored in an external authentication system;
a plurality of buttons wherein each button is assigned a unique account identification number representing an account for conducting a commercial transaction, and said buttons for selecting and dispensing a previously unused number from the set of random numbers using the software and
displaying means for displaying the dispensed numbers and said unique account identification numbers.

11. The system for conducting commercial transactions according to claim 10 further including a communications port, wherein the system may be reprogrammed via the communications port with a new set of random numbers by an external system when the unique set of random numbers becomes exhausted.

12. The system for conducting commercial transactions according to claim 11, wherein the communications port may be connected to at least one of the Internet and a cellular network.

13. The system for conducting commercial transactions according to claim 10 further including 1 to N predetermined polynomial transformation equations, wherein the 1 to N predetermined polynomial transformation equations operate on each random number to provide 1 to N additional numbers for each of the predetermined random numbers.

14. The system for conducting commercial transactions according to claim 10 further including a PIN number, wherein the software is configured to request a user to enter the predetermined PIN number each time the system is activated, and wherein the software is configured to not dispense a random number until the correct PIN number has been entered.

15. A code dispensing device comprising:
a power source,
first memory for storing a unique set of predetermined random numbers;
second memory storing software when executed causes the code dispensing device to perform the steps of: selecting and dispensing an unused number from the set of random numbers, wherein the set of random numbers is identical to a set of numbers stored in an external authentication system;
a plurality of buttons wherein each button is assigned a unique account identification number representing an account for conducting a commercial transaction;
means for selecting and dispensing a previously unused number from the set of random numbers using the software and
displaying means for displaying the dispensed numbers and said unique account identification numbers.

16. The code dispensing device according to claim 15, further comprising:
a power source for powering the dispensing device.

17. The code dispensing device according to claim 16, wherein said power source includes a photo-electric device.

18. The code dispensing device according to claim 15, further comprising:
indicator means for indicating to a user of the dispensing device an amount of undispensed codes remaining in the storage means.

19. The code dispensing device according to claim 15, wherein each code is only dispensed once.

* * * * *